US00PP22360P2

(12) United States Plant Patent
Pineau

(10) Patent No.: US PP22,360 P2
(45) Date of Patent: Dec. 20, 2011

(54) ***ABELIA* PLANT NAMED 'MINEDWARD'**

(50) Latin Name: *Abelia×grandiflora*
Varietal Denomination: Minedward

(75) Inventor: Patrick Pineau, Beaufort en Vallée (FR)

(73) Assignee: Pépinières Minier, Beaufort-en-Vallée (FR)

( * ) Notice: Subject to any disclaimer, the term of this patent is extended or adjusted under 35 U.S.C. 154(b) by 0 days.

(21) Appl. No.: 12/807,825

(22) Filed: Sep. 14, 2010

(51) Int. Cl.
*A01H 5/00* (2006.01)

(52) U.S. Cl. ..... Plt./226

(58) Field of Classification Search ..... Plt./226
See application file for complete search history.

(56) References Cited

OTHER PUBLICATIONS

Upov Plant Variety Database 2011/03 p. 1.*

* cited by examiner

*Primary Examiner* — Annette Para
(74) *Attorney, Agent, or Firm* — C. A. Whealy

(57) ABSTRACT

A new and distinct cultivar of *Abelia* plant named 'Minedward', characterized by its compact and rounded plant habit; freely branching habit; dense and bushy growth habit; freely and continuous flowering habit; long flowering period; light lavender-colored flowers; and good garden performance.

2 Drawing Sheets

Botanical designation: *Abelia×grandiflora.*
Cultivar denomination: 'MINEDWARD'.

BACKGROUND OF THE INVENTION

The present invention relates to a new and distinct cultivar of *Abelia* plant, botanically known as *Abelia×grandiflora* and hereinafter referred to by the name 'Minedward'.

The new *Abelia* is a product of a planned breeding program conducted by the Inventor in La Ménitré, Maine et Loire, France. The objective of the breeding program was to develop new compact and freely flowering *Abelia* plants with attractive flower coloration.

The new *Abelia* plant originated from a self-pollination in July, 2003 of *Abelia×grandiflora* 'Edward Goucher', not patented. The new *Abelia* plant was discovered and selected by the Inventor in October, 2004 as a single flowering plant within the progeny of the stated self-pollination in a controlled environment in La Ménitré, Maine et Loire, France.

Asexual reproduction of the new *Abelia* plant by semi-hardwood cuttings in a controlled greenhouse environment in La Ménitré, Maine et Loire, France since October, 2004 has shown that the unique features of this new *Abelia* plant are stable and reproduced true to type in successive generations of asexual reproduction.

SUMMARY OF THE INVENTION

Plants of the new *Abelia* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Minedward'. These characteristics in combination distinguish 'Minedward' as a new and distinct cultivar of *Abelia* plant:

1. Compact and rounded plant habit.
2. Freely branching habit; dense and bushy growth habit.

3. Freely and continuous flowering habit.
4. Long flowering period.
5. Light lavender-colored flowers.
6. Good garden performance.

Plants of the new *Abelia* can be compared to plants of the parent, 'Edward Goucher'. In side-by-side comparisons, plants of the new *Abelia* differ primarily from plants of 'Edward Goucher' in the following characteristics:

1. Plants of the new *Abelia* are more compact than plants of 'Edward Goucher'.
2. Plants of the new *Abelia* grow slower than plants of 'Edward Goucher'.
3. Plants of the new *Abelia* are more freely branching than plants of 'Edward Goucher'.
4. Plants of the new *Abelia* are more freely flowering than plants of 'Edward Goucher'.
5. Plants of the new *Abelia* have lighter green-colored leaves than plants of 'Edward Goucher'.
6. Plants of the new *Abelia* flower for a longer period of time than plants of 'Edward Goucher'.
7. Plants of the new *Abelia* and 'Edward Goucher' differ in flower color.

Plants of the new *Abelia* can be compared to plants of an unnamed selection of *Abelia×grandiflora*, not patented. In side-by-side comparisons plants of the new *Abelia* differ from plants of the unnamed selection in the following characteristics:

1. Plants of the new *Abelia* are more compact than plants of the unnamed selection.
2. Plants of the new *Abelia* are not as vigorous as plants of the unnamed selection.
3. Plants of the new *Abelia* are more freely branching than plants of the unnamed selection.
4. Plants of the new *Abelia* and the unnamed selection differ in flower color as plants of the unnamed selection have white-colored flowers.

BRIEF DESCRIPTION OF THE PHOTOGRAPHS

The accompanying colored photographs illustrate the overall appearance of the new *Abelia* plant showing the colors as true as it is reasonably possible to obtain in colored reproductions of this type. Colors in the photographs may differ slightly from the color values cited in the detailed botanical description which accurately describe the colors of the new *Abelia* plant.

The photograph on the first sheet is a top perspective view of a typical plant of 'Minedward' grown in an outdoor nursery.

The photograph on the second sheet is a close-up view of a typical flowering plant of 'Minedward'.

DETAILED BOTANICAL DESCRIPTION

The aforementioned photographs and following observations, measurements and values describe plants grown in Grand Haven, Mich. during the spring and summer in an outdoor nursery and under conditions which closely approximate commercial *Abelia* production. Plants were two years old when the photographs and the description were taken. In the description, color references are made to The Royal Horticultural Society Colour Chart, 2001 Edition, except where general terms of ordinary dictionary significance are used.

Botanical classification: *Abelia×grandiflora* 'Minedward'.

Parentage:

*Female, or seed, parent.*—*Abelia×grandiflora* 'Edward Goucher', not patented.

*Male, or pollen, parent.*—*Abelia×grandiflora* 'Edward Goucher', not patented.

Propagation:

*Type.*—By semi-hardwood cuttings.

*Time to initiate roots, summer.*—About seven weeks at 16° C.

*Time to produce a rooted young plant, summer.*—About ten weeks at 16° C.

*Root description.*—Fine, fleshy; white in color.

*Rooting habit.*—Moderate branching; low density.

Plant description:

*Plant form and growth habit.*—Perennial shrub; compact and rounded plant habit; moderate vigorous growth habit.

*Branching habit.*—Freely branching habit, dense and bushy growth habit, about 85 lateral branches develop per plant; pinching enhances lateral branch development.

*Plant height.*—About 50 cm.

*Plant diameter* (*area of spread*).—About 75 cm.

Lateral branch description:

*Length.*—About 22 cm.

*Diameter.*—About 1.5 mm.

*Internode length.*—About 2.5 cm.

*Aspect.*—Upright to outwardly spreading.

*Texture, developing.*—Smooth, glabrous.

*Texture, developed.*—Woody.

*Color.*—Developing: Close to 184A. Fully developed: Close to 197C.

Foliage description:

*Arrangement.*—Opposite, simple.

*Length.*—About 2.4 cm.

*Width.*—About 1.2 cm.

*Shape.*—Ovate.

*Apex.*—Acute.

*Base.*—Obtuse.

*Margin.*—Entire.

*Texture, upper and lower surfaces.*—Smooth, glabrous.

*Venation pattern.*—Pinnate.

*Color.*—Developing leaves, upper surface: Close to 141A. Developing leaves, lower surface: Close to 141B. Fully expanded leaves, upper surface: Close to 139A to 139B; venation, close to 139A to 139B. Fully expanded leaves, lower surface: Close to 137C; venation, close to 137C.

*Petiole.*—Length: About 2 mm. Diameter: About 1 mm. Texture, upper and lower surfaces: Smooth, glabrous. Color, upper and lower surfaces: Close to 137C.

Flower description:

*Flower appearance/arrangement.*—Single funnelform flowers arranged on terminal and axillary panicles; freely flowering habit with about twelve flowers per inflorescence.

*Fragrance.*—Fragrant, pleasant.

*Flower longevity.*—Flowers last for about two weeks on the plant; flowers not persistent.

*Natural flowering season.*—Long flowering period, plants flower continuously from July to October in Michigan.

*Inflorescence height.*—About 6 cm.

*Inflorescence width.*—About 5 cm.

*Flower diameter.*—About 2 cm.

*Flower depth.*—About 2.5 cm.

*Flower bud.*—Length: About 1 cm. Diameter: About 5 mm. Shape: Oblanceolate. Color: Close to 143C.

*Petals.*—Arrangement/quantity: Single whorl of five fused petals. Lobe length: About 7 mm. Lobe width: About 7 mm. Shape: Roughly spatulate. Apex: Obtuse. Margin: Entire. Texture, upper and lower surfaces: Smooth, glabrous. Color: When opening and fully opened, upper surface: Close to 84D and 75C; color becoming closer to 155C with development. When opening and fully opened, lower surface: Close to 84D and 75C.

*Sepals.*—Quantity/arrangement: Five; three are fused; calyx, cruciform. Length: About 1 cm. Width: About 5 mm. Shape: Elliptical. Apex: Obtuse. Base: Obtuse. Margin: Entire. Texture, upper and lower surfaces: Smooth, glabrous. Color: Developing, upper surface: Close to 143A. Developing, lower surface: Close to 143B. Fully developed, upper surface: Close to 143B tinged with close to 181C. Fully developed, lower surface: Close to 143B.

*Peduncles.*—Length: About 3 cm. Diameter: About 1 mm. Strength: Strong, flexible. Texture: Smooth, glabrous. Angle: Mostly upright. Color: Close to 143A.

*Pedicels.*—Length: About 7 mm. Diameter: About 1 mm. Strength: Strong, flexible. Texture: Smooth, glabrous. Angle: About 30° to 40°. Color: Close to 143A.

*Reproductive organs.*—Stamens: Quantity per flower: Four. Anther length: About 1.5 mm. Anther shape: Oblong to elliptical. Anther color: Close to 155A. Pollen amount: Scarce. Pollen color: Close to 155C. Pistils: Quantity per flower: One. Pistil length: About 1.4 cm. Stigma shape: Globular. Stigma color: Close to 155C. Style length: About 1.3 cm. Style color: Close to 155A. Ovary color: Close to 155A. Seeds: Length: Less than 1 mm. Diameter: Less than 1 mm. Color: Brown.

Garden performance: Plants of the new *Abelia* have been observed to have good garden performance and to tolerate rain, wind and to tolerate temperatures ranging from −10° C. to 40° C.

Pathogen/pest resistance: Plants of the new *Abelia* have not been shown to be resistant to pathogens and pests common to *Abelia*.

It is claimed:

1. A new and distinct *Abelia* plant named 'Minedward' as illustrated and described.

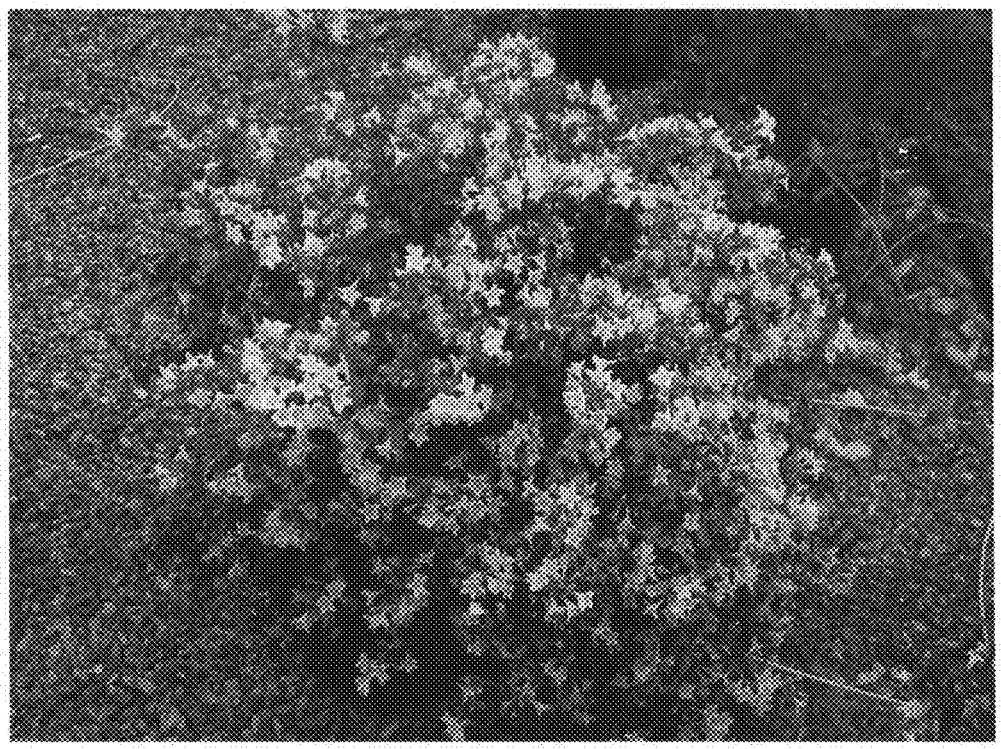

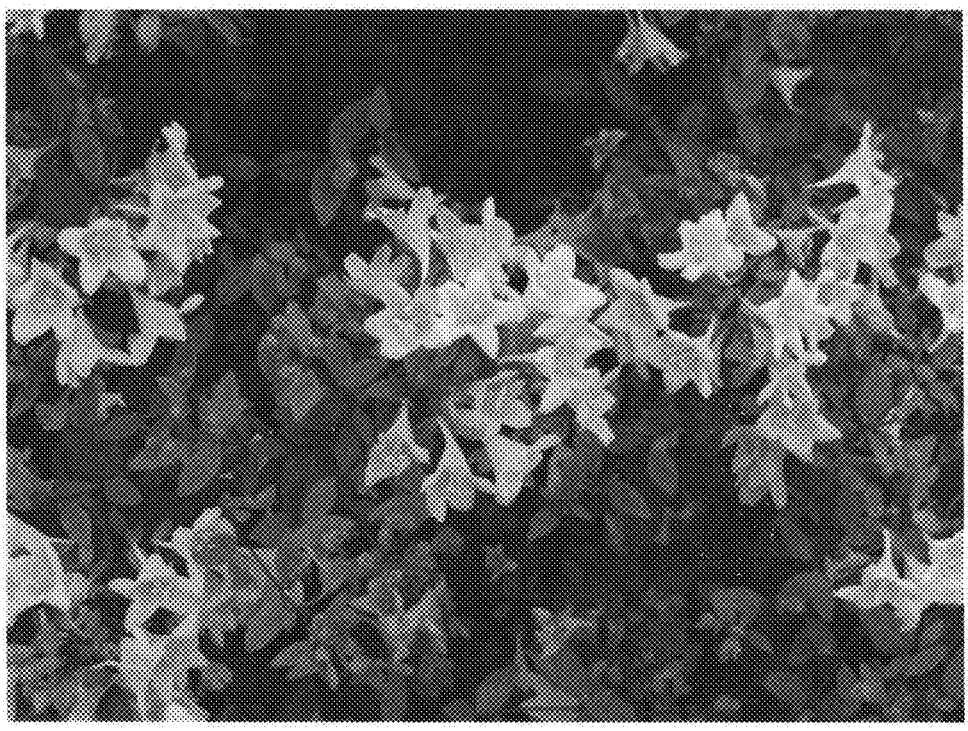

* * * * *